US011617892B2

(12) United States Patent
Iyer et al.

(10) Patent No.: US 11,617,892 B2
(45) Date of Patent: Apr. 4, 2023

(54) TOOLLESS LEAD CONNECTOR ASSEMBLY

(71) Applicant: Medtronic, Inc., Minneapolis, MN (US)

(72) Inventors: Rajesh V. Iyer, Eden Prairie, MN (US); Randy S. Roles, Elk River, MN (US); Erik R. Scott, Maple Grove, MN (US); Andrew J. Thom, Maple Grove, MN (US)

(73) Assignee: Medtronic, Inc., Minneapolis, MN (US)

( * ) Notice: Subject to any disclaimer, the term of this patent is extended or adjusted under 35 U.S.C. 154(b) by 574 days.

(21) Appl. No.: 16/604,383

(22) PCT Filed: Mar. 14, 2018

(86) PCT No.: PCT/US2018/022431
§ 371 (c)(1),
(2) Date: Oct. 10, 2019

(87) PCT Pub. No.: WO2018/194770
PCT Pub. Date: Oct. 25, 2018

(65) Prior Publication Data
US 2020/0155853 A1    May 21, 2020

Related U.S. Application Data

(60) Provisional application No. 62/488,399, filed on Apr. 21, 2017.

(51) Int. Cl.
*A61N 1/375* (2006.01)
*H01R 13/52* (2006.01)
*H01R 13/59* (2006.01)

(52) U.S. Cl.
CPC ....... *A61N 1/3752* (2013.01); *H01R 13/5224* (2013.01); *H01R 13/59* (2013.01)

(58) Field of Classification Search
CPC ... A61N 1/3752; H01R 13/5224; H01R 13/59
See application file for complete search history.

(56) References Cited

U.S. PATENT DOCUMENTS 4,934,366 A * 6/1990 Truex ................. A61N 1/3752
607/37
5,766,042 A    6/1998 Ries et al.
(Continued)

FOREIGN PATENT DOCUMENTS

WO    WO 1998/057702 A1    12/1998
WO    WO 2018/194770 A2    10/2018

OTHER PUBLICATIONS

International Patent Application No. PCT/US2018/022431, filed Mar. 14, 2018; International Search Report / Written Opinion dated Jan. 18, 2019; 16 pages.

*Primary Examiner* — Thomas Sweet
(74) *Attorney, Agent, or Firm* — Mueting Raasch Group

(57) ABSTRACT

A lead connector assembly includes a lead receptacle, a sleeve, and a handle for coupling to a medical lead. The lead receptacle has an inner surface and an opening configured to receive the lead. The sleeve is deflectable by the inner surface of the lead receptacle. The sleeve has a distal end portion defining a first outer diameter to engage the lead in a locked position and a second outer diameter greater than the first diameter in an unlocked position. The handle is coupled to the lead receptacle and a proximal end portion of the sleeve to move the sleeve axially in both directions along the longitudinal axis relative to the lead receptacle. The lead connector assembly retains the lead in the locked position. The lead receptacle is couplable to a medical device housing.

20 Claims, 9 Drawing Sheets

(56) References Cited

U.S. PATENT DOCUMENTS

| | | | |
|---|---|---|---|
| 6,080,188 A * | 6/2000 | Rowley | H01R 4/5008 607/36 |
| 6,312,297 B1 | 11/2001 | Lorkowski | |
| 6,428,368 B1 | 8/2002 | Hawkins et al. | |
| 2010/0029127 A1 | 2/2010 | Sjostedt | |
| 2016/0129267 A1 | 5/2016 | Thom et al. | |

* cited by examiner

TOOLLESS LEAD CONNECTOR ASSEMBLY

RELATED APPLICATION

This application is the § 371 U.S. National Stage of International Application No. PCT/US2018/022431, filed Mar. 14, 2018, which claims the benefit of U.S. Provisional Application Ser. No. 62/488,399, filed Apr. 21, 2017, which are incorporated by reference.

TECHNICAL FIELD

Embodiments relate to connecting medical leads to medical devices. More particularly, embodiments relate to a lead connector assembly including an integrated deflectable structure to provide fixation of a medical lead inserted into a medical device.

BACKGROUND

Medical devices that provide a medical function, such as electrical stimulation, are often affixed to the body at a position of convenience. This is particularly true for implantable medical devices where the device is implanted in a convenient location that may be some distance from a target site within the body where the medical therapy is to be applied. A medical lead is attached to the medical device and is routed to the target site within the body.

The medical lead for electrical stimulation provides electrical contacts on one end and electrodes on another end with conductors inside a lead body where those conductors interconnect contacts to the electrodes that are in contact with the body tissue. The lead is typically attached to the medical device by the contact end of the lead being inserted into a bore within a lead connector assembly of the medical device, which may be a header block. The contacts of the lead become electrically coupled to electrical connectors within the header block so that stimulation signals pass from the electrical connectors to the contacts and then through the conductors to the electrodes.

To fix the lead within the bore, a set screw may be used within a set screw block of the header block and tightened onto a metal ring on the contact end of the medical lead that is present within the bore of the header block. While the set screw adequately fixes the position of the contact end of the lead within the bore of the header block, using a set screw for lead fixation presents some drawbacks. For instance, in most cases a clinician must use a tool to tighten the set screw because the set screw cannot be adequately gripped and because the set screw becomes countersunk within the set screw block as the set screw is tightened. The set screw presents a connection that may allow fluid ingress into the header block (for example, due to distortion of the lead sleeve).

Furthermore, the set screw and other threaded coupling techniques may overtighten and distort the sleeve of the lead to retain the lead. This may disturb the desired arrangement of structures within the lead, such as the lumens and conductors extending therethrough.

SUMMARY

Various aspects of the present disclosure relate to a medical device having a lead receptacle, a sleeve, and a handle. The lead receptacle includes an inner surface and defining an opening configured to receive a lead. The sleeve is deflectable by the inner surface of the lead receptacle. The sleeve has a proximal end portion and a distal end portion. The distal end portion defines a first outer diameter to engage the lead in a locked position and a second outer diameter greater than the first diameter in an unlocked position. The handle is coupled to the lead receptacle and the proximal end portion of the sleeve to move the sleeve axially in both directions along the longitudinal axis relative to the lead receptacle.

Various other aspects of the present disclosure relate to a medical system having a lead, a lead receptacle, a sleeve, and a handle. The lead includes a sleeve and a collar fixed to the sleeve. The lead receptacle defines an opening configured to receive the lead. The sleeve is deflectable by the inner surface of the lead receptacle. The sleeve has a proximal end portion and a distal end portion. The distal end portion defines a first outer diameter to engage the collar of the lead in a locked position and a second outer diameter greater than the first diameter in an unlocked position. The handle is coupled to the lead receptacle and the proximal end portion of the sleeve to move the sleeve axially in both directions along the longitudinal axis relative to the lead receptacle.

Various further aspects of the present disclosure relate to a medical system having a lead receptacle, a lead, a sleeve, and a handle. The lead receptacle defines an opening. The lead has a sleeve extending through the opening and a collar fixed to the sleeve. The sleeve is deflectable by the inner surface of the lead receptacle and comprising a proximal end portion and a distal end portion defining a first outer diameter to engage the lead in a locked position and a second outer diameter greater than the first diameter in an unlocked position. The handle is coupled to the lead receptacle and the proximal end portion of the sleeve to move the sleeve axially in both directions along the longitudinal axis relative to the lead receptacle.

It is to be understood that both the foregoing general description and the following detailed description present embodiments of the subject matter of the present disclosure, and are intended to provide an overview or framework for understanding the nature and character of the subject matter of the present disclosure as it is claimed.

Figure 1:
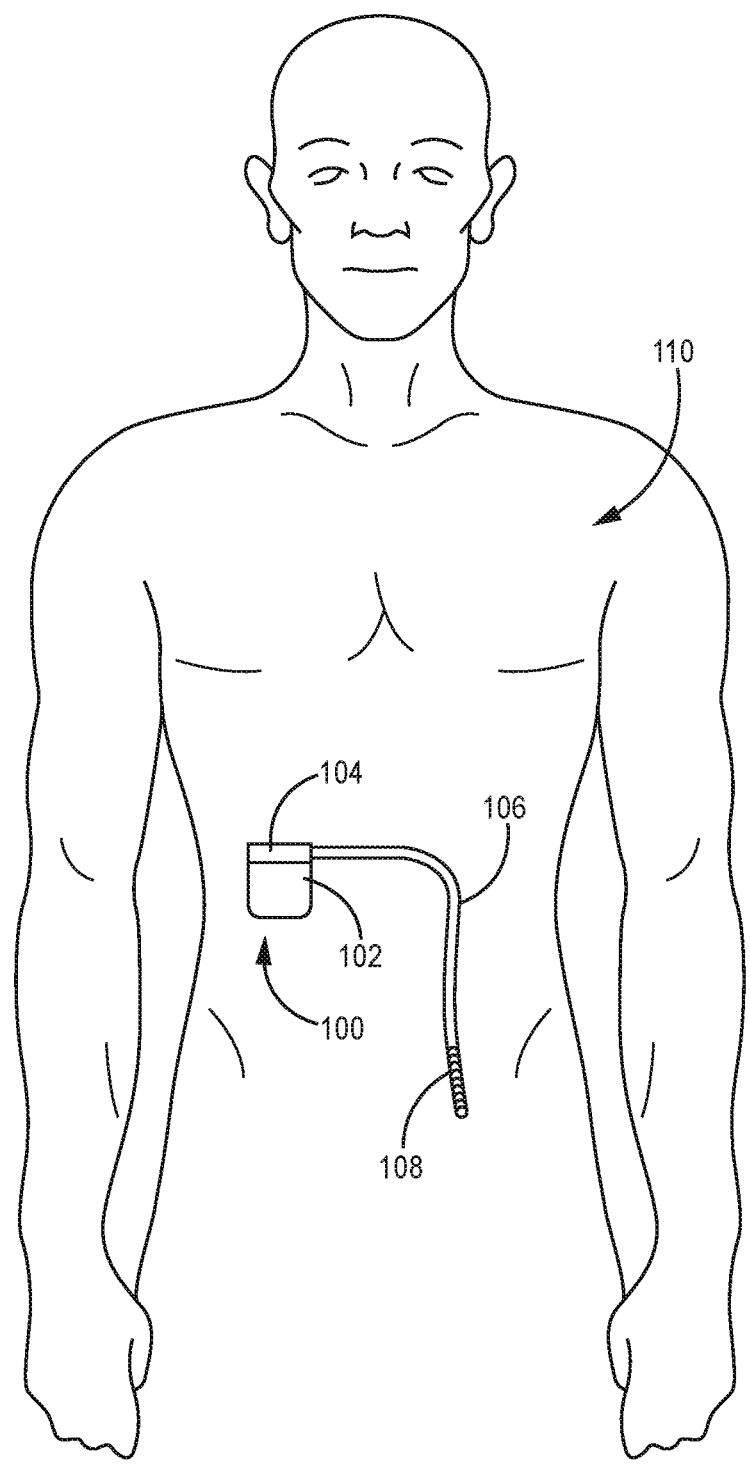
FIG. 1 shows an operating environment for a medical system including a medical device with a lead connector assembly and a medical lead attached to or implanted into a patient.

The disclosure may be more completely understood in consideration of the following detailed description of various embodiments of the disclosure and the accompanying drawings.

DETAILED DESCRIPTION

Embodiments of the present disclosure provide a lead connector assembly including a sleeve coupled to a handle that can move the sleeve axially (for example, longitudinally) relative to a lead receptacle. In particular, the handle can move the sleeve axially in both directions. Moving the sleeve in a distal, axial direction may deflect the sleeve against the lead receptacle to engage a collar on a lead inserted into the lead receptacle. The sleeve can apply an axial force against the collar to retain and provide a seal. The sleeve can also a radial (for example, lateral) force on the collar. Moving the sleeve in a proximal, axial direction may disengage the sleeve from the lead receptacle and the collar, which may further allow the sleeve to revert to a nominal shape. As used herein, the term "proximal" refers to the direction of a lead being removed from the lead connector assembly and the term "distal" refers to the opposite direction (for example, the lead being inserted into the lead connector assembly). The nominal shape of the sleeve may facilitate an easy insertion of a subsequent lead. Further, the rotation of the handle may be limited, which may prevent distortion of the lead due to overtightening and unintentional radial overcompression. The lead can maintain concentricity within the lead connector assembly. Furthermore, the handle, sleeve, and lead receptacle may all be integrated such that, once assembled, one component is not easily removed from the others during use of the lead connector assembly.

Reference will now be made to the drawings, which depict one or more aspects described in this disclosure. However, it will be understood that other aspects not depicted in the drawings fall within the scope and spirit of this disclosure. Like numbers used in the figures refer to like components, steps and the like. However, it will be understood that the use of a reference character to refer to an element in a given figure is not intended to limit the element in another figure labeled with the same reference character. In addition, the use of different reference characters to refer to elements in different figures is not intended to indicate that the differently referenced elements cannot be the same or similar.

FIG. 1 shows an environment 110 for a medical system 100 that includes a medical device 102 and a medical lead 106. In this example, the medical system 100 including the medical device 102 and the lead 106 are implantable. The lead 106 includes a proximal end that has been inserted into a bore of a header block 104 of the medical device 102. The distal end of the lead 106 includes electrodes 108 that are positioned at a target site where electrical stimulation therapy is to be provided.

Figure 2:
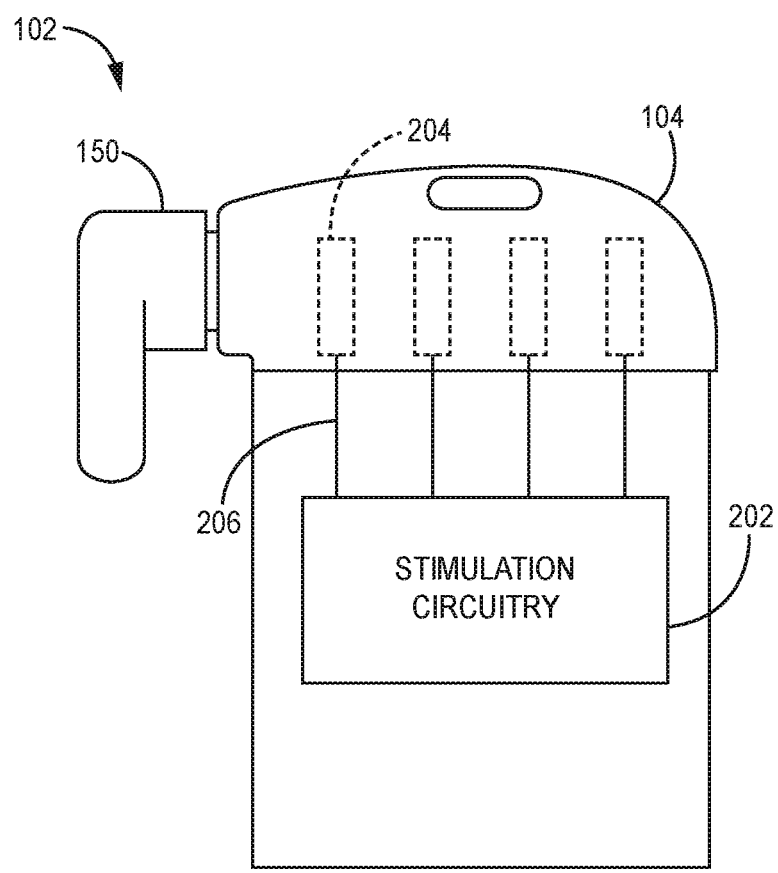
FIG. 2 shows an example medical device having an example lead connector assembly that can be manipulated to provide a lead fixation.

FIG. 2 shows an example of the medical device 102 and a header block 104 of the medical device 102. The header block 104 may be a separate assembly that is mounted to the medical device 102 or may be integral to the medical device 102 via a common housing. The medical device 102 of this example includes stimulation circuitry 202 that provides electrical stimulation signals via a set of feedthrough conductors 206 that interconnect with corresponding electrical connectors 204 inside of the header block 104. The electrical connectors 204 may also be described conductive contacts or pressure contacts. The medical device 102 of this example also includes a lead connector assembly 150 that can be grasped and manipulated by a clinician, and thus by hand and without tools, when connecting a lead 106 to the header block 104 of the medical device 102. The lead connector assembly 150 may also be described as, or described as integral with or coupled to, a connector, connector block, header, or header block.

Figure 3A:
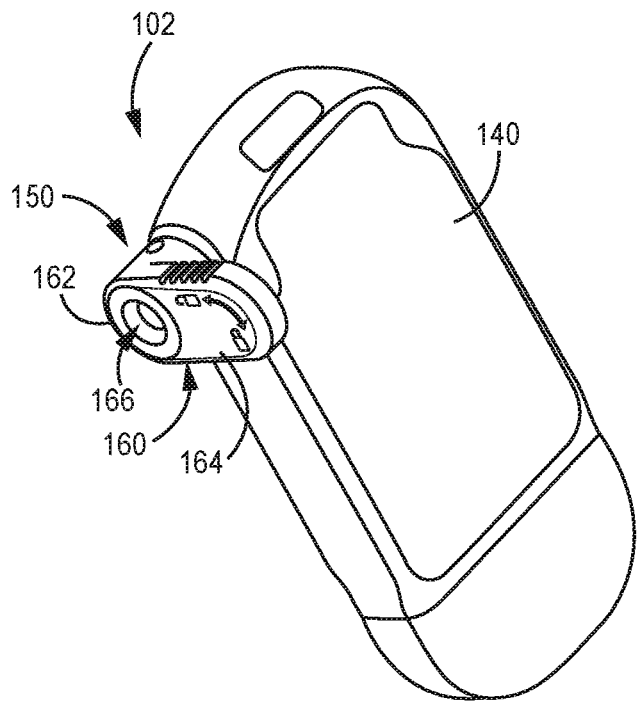
FIGS. 3A-B show perspective views of an example medical device with an example lead connector assembly in unlocked and locked positions.
Figure 3B:
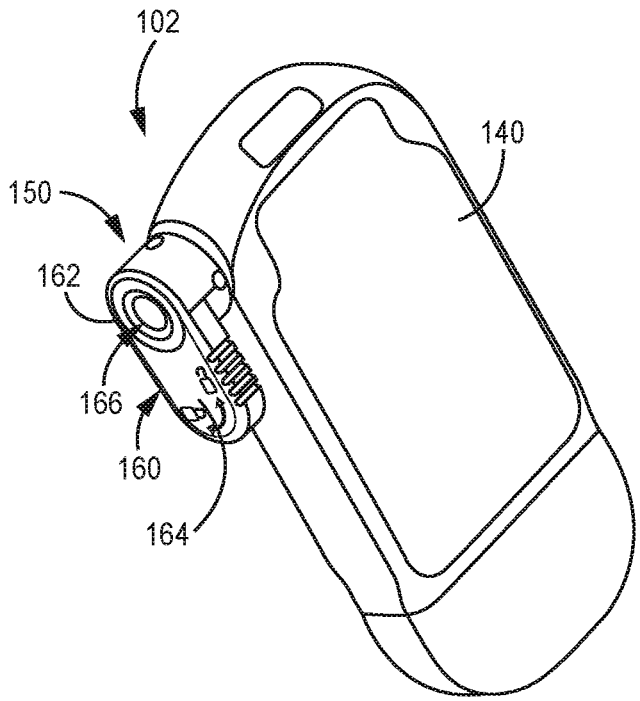

FIGS. 3A-B show perspective views of the example medical device 102 having a housing 140 and the lead connector assembly 150. The lead connector assembly 150 in this example medical device 102 protrudes or extends outwardly from the housing 140.

The lead connector assembly 150 may include a handle 160. The handle 160 may protrude or extend outwardly from the housing 140. In the illustrated embodiment, the handle 160 protrudes or extends outwardly from the housing 140 in a first direction and extends outwardly from the housing and a second direction.

The handle 160 may include an axial portion 162 and a lever portion 164. In some embodiments, the axial portion 162 extends outwardly from the housing 140 in the first direction and the lever portion 164 extends outwardly from the housing in the second direction.

Figure 6:
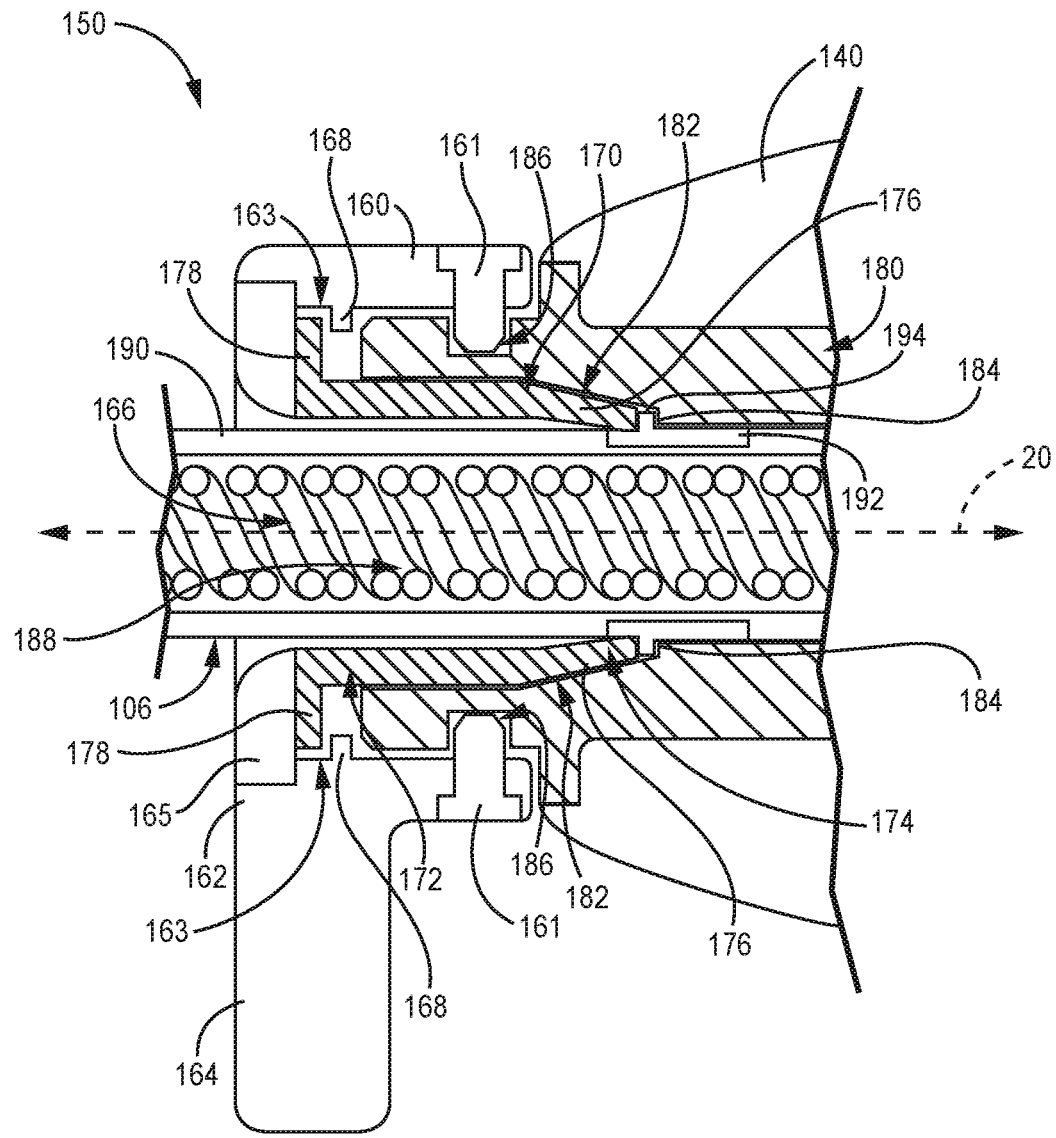

The axial portion 162 may define an opening 166 to receive the lead 106 (FIGS. 1 and 6). The lever portion 164 may facilitate an easy grip for a user to lock and unlock the lead connector assembly 150. The locked position preferably couples the lead 106 to the medical device 102 for retention, whereas the unlocked position preferably uncouples the lead 106 from the medical device 102 for removal.

The handle 160 may be rotated to lock and unlock the lead connector assembly 150. In some embodiments, the lead connector assembly 150 may define a limited rotation of the handle 160 relative to other parts of the medical device 102. The limited rotation may provide a simple manipulation for the user to lock and unlock the lead connector assembly 150. The limited rotation may limit the force applied to the lead 106, which may mitigate adverse effects on the lead due to excessive radial compression (for example, excess energy expended by the user and plastic deformation of components). Further, the limited rotation may prevent the handle 160 or other parts of the lead connector assembly 150 from being removed or uncoupled from the housing 140, the lead 106, or other parts of the medical device 102, which may facilitate simple handling to retain or release the lead 106 from the medical device 102.

In some embodiments, the handle 160 rotates no more than one full rotation or about 360 degrees between a fully locked and a fully unlocked position. In some embodiments, the handle 160 rotates no more than about 270 degrees, about 180 degrees, about 120 degrees, about 90 degrees, about 60 degrees, about 45 degrees, about 30 degrees, or less.

Figure 4:
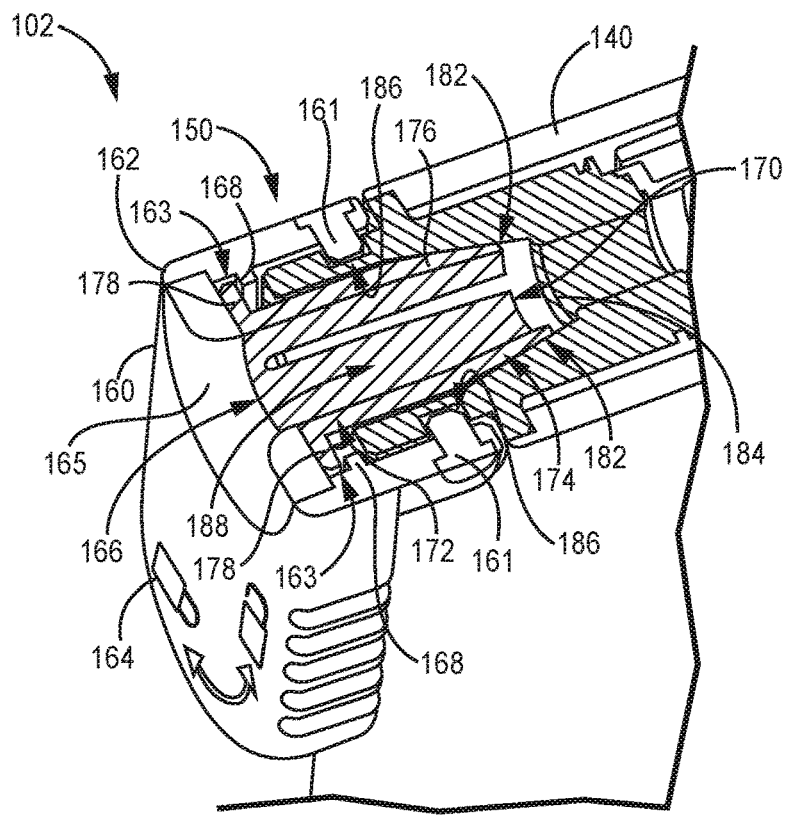
FIGS. 4-6 show various views of components of an example lead connector assembly in locked and unlocked positions.
Figure 5:
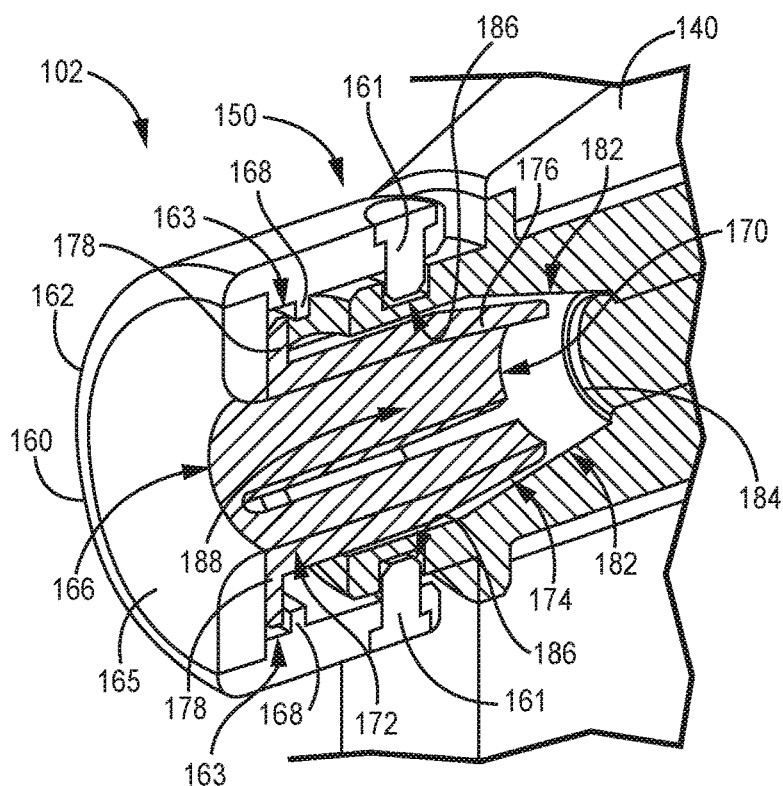

FIGS. 4-6 show various views of example lead connector assembly 150 in locked and unlocked positions coupled to a housing 140. FIG. 4 shows a cutaway, perspective view of the lead connector assembly 150 in a locked position. FIG. 5 shows a cutaway, perspective view of the lead connector assembly 150 in an unlocked position. FIG. 6 shows a cross-section view of the lead connector assembly 150 in a locked position to retain the lead 106.

In the illustrated embodiment, the example lead connector assembly 150 includes the handle 160, the sleeve 170, and the lead receptacle 180. The sleeve 170 may be disposed between the handle 160 in the lead receptacle 180. The sleeve 170 may be described as housed by, or within, at least partially, the handle 160 and the lead receptacle 180. The handle 160 may be coupled to the lead receptacle 180. In some embodiments, once coupled, the handle 160 may not be removable from the lead receptacle 180. In other words, the handle 160 may rotate between a fully locked position and a fully unlocked position without the sleeve 170, or the handle 160, being removable from the lead receptacle 180. The lead connector assembly 150 may operate as one integrated unit.

In the illustrated embodiment, the lead 106 extends along a longitudinal axis 20. The lead 106 may extend through the lead connector assembly 150 and be retained by the lead connector assembly 150. For example, the lead 106 may extend through a bore defined by the components of the lead connector assembly 150 and be retained within the lead connector assembly 150. The bore may also be aligned to extend along the longitudinal axis 20.

The lead 106 may include a lead sleeve 190 and a collar 192 coupled to the lead sleeve. The collar 192 may define a shoulder 194. The shoulder 194 may protrude between the sleeve 170 and the lead receptacle 180. The collar 192 may be engaged by the sleeve 170 to retain the lead 106 within the lead connector assembly 150. In some embodiments, the shoulder 194 of the collar 192 is axially compressed between the sleeve 170 and the lead receptacle 180 in the locked position to retain the lead 106 within the lead connector assembly 150.

In some embodiments, the collar 192 is formed of a rigid material. For example, the collar 192 may be formed of a rigid plastic, a rigid metal, or other suitable rigid material. The collar material may be described as incompressible or have a sufficient resilience to deflection or deformation in response to any radial forces used to retain the lead 106 in the lead connector assembly 150. Radial forces may not be required to seal the collar 192 to the lead connector assembly 150. Any radial forces present may be unintentional. In some embodiments, radial forces may be intentional.

The lead connector assembly 150 may be coupled to the housing 140. The lead receptacle 180 may form a hermetic seal with the housing 140. In some embodiments, the lead receptacle 180 is hermetically coupled to the housing 140 using, for example, various known techniques. In some embodiments, the lead receptacle 180 is integrally formed with the housing 140. For example, the lead receptacle 180 and housing 140 may be formed from a single piece of plastic. In some embodiments, the lead receptacle 180 is coupled to the housing 140 using a set screw extending through the housing and engaging the lead receptacle 180. Coupling with the set screw may not form a hermetic seal between the lead receptacle 180 and the housing 140.

The components of the lead connector assembly 150 may be formed of any suitable material. In some embodiments, one or more components may be formed of a plastic. In some embodiments, one or more components may be formed of a metal (for example, titanium). In some embodiments, the sleeve 170 is formed of a resilient material that may deflect without being plastically deformed. For example, the sleeve 170 may be formed of a resilient material capable of being deflected and returning to the nominal shape. The sleeve 170 may be formed of a material that is resilient and rigid (for example, not compressible). The resilient material may be formed, for example, of metal or plastic. Non-limiting examples of metal materials include titanium (for example, commercially pure titanium or alloy, such as Grade 5), MP35N, and stainless steel (300 series, such as 316). Non-limiting examples of plastic materials include Delrin® and polysulfone.

In the illustrated embodiment, the lead connector assembly 150 includes one handle 160, one sleeve 170, and one lead receptacle 180. Additional lead connector assemblies 150, or components thereof, may be included to receive additional leads 106. For example, another lead receptacle 180 may be included to receive another lead 106.

As shown, the example handle 160 includes the axial portion 162, the lever portion 164, the opening 166, an inward annular protrusion 168, an inward protrusion 161, a channel 163, and a cap 165. The lead 106 may extend through the handle 160 in a longitudinal direction. The opening 166 may be defined by the axial portion 162 along the longitudinal axis 20. The opening 166 may form part of the bore to receive the lead 106. As shown, the lead 106 may extend through the opening 166. The lever portion 164 may extend radially from the axial portion 162, or orthogonally from the longitudinal axis 20. The lever portion 164 may be shaped and sized to be easily manipulated by the user.

The lever portion 164 may protrude a lesser distance from the axial portion 162 when the medical device 102 includes more than one lead connector assembly 150. The lead connector assemblies 150 may be adjacent to or in proximity to one another. The lever portion 164 preferably does not interfere with the operation of another lever portion. In some embodiments, the lever portion 164 is optional, and the user may directly manipulate the axial portion 162.

The channel 163 may be used in cooperation with a feature of the sleeve to couple the handle 160 to the sleeve 170. In some embodiments, the channel 163 is formed between the cap 165 and the inward annular protrusion 168. The channel 163 may define a floating connection with the sleeve 170. The inward annular protrusion 168 may extend inwardly from the axial portion 162 and into the opening 166 or the bore (for example, toward the longitudinal axis 20). The inward annular protrusion 168 may be integrally formed from the material of the axial portion 162.

The one or more inward annular protrusions 168 may be described as a shoulder. In the illustrated embodiment, one inward annular protrusion 168 is shown that is disposed around an inner surface of the axial portion 162 defined by the opening 166. The inward annular protrusion 168 may extend only partially around the inner surface of the axial portion 162. In the illustrated embodiment, the inward annular protrusion 168 is continuous. The inward annular protrusion 168 may include one or more discrete protrusions.

The inward protrusion 161 may be used in cooperation with a feature of the lead receptacle 180 to guide the handle 160 relative to the lead receptacle 180. In some embodiments, the inward protrusion 161 may be inserted into the axial portion 162. In other embodiments, the inward protrusion 161 is integrally formed from the material of the axial portion 162. The inward annular protrusion 161 may include a pin, a ball spring, or any other suitable structure for guiding the handle 160.

The inward protrusion 161 may include one or more discrete protrusions. In the illustrated embodiment, two inward protrusions 161 are shown. In some embodiments, only one inward protrusion 161 is included. In other embodiments, three, four, five, or more inward protrusions 161 are included. The one or more inward protrusions 161 may be disposed around an inner surface of the axial portion 162 defined by the opening 166.

As shown, the example lead receptacle 180 includes an inner surface 182, a shoulder 184 of the inner surface 182, an outward slot 186, and an opening 188. The lead 106 may extend through the lead receptacle 180 in a longitudinal direction. The inner surface 182 may extend distally from the opening 188. The opening 188 may be wide enough (for example, in diameter) to concurrently receive the lead 106 and the sleeve 170. The opening 188 may form part of the bore to receive the medical lead 106. The inner surface 182 may be tapered. For example, the inner surface 182 may be tapered from a proximal end to a distal end along the longitudinal axis 20. The inner surface 182 may be in the shape of a cone, or partial cone. A shoulder 184 may be formed on the inner surface 182. The shoulder 184 may be disposed adjacent to, in proximity to, or at a distal end of the inner surface 182. The inner surface 182 may engage the sleeve 170, particularly an outer surface thereof, disposed within the lead receptacle 180.

The lead receptacle 180 may limit the movement of handle 160. In some embodiments, the lead receptacle 180 limits the movement of the handle 160 from extending axially or rotating beyond at least one of the fully locked and unlocked positions.

The lead receptacle 180 may define the slot 186 to engage the inward protrusion 161 of the handle 160. The slot 186 may define the locked and unlocked positions at a first end and a second end. The slot 186 may be formed in the material of the lead receptacle 180 on the outward surface of the lead receptacle. The inward protrusion 161 may slide along the slot 186.

The slot 186 may be any suitable shape and size that allows the handle 160 to rotate between locked and unlocked positions. In some embodiments, the slot 186 may guide the inward protrusion 161 rotationally and axially. For example, the slot 186 may guide the inward protrusion 161 axially in a distal direction in response to the handle 160 rotating clockwise and proximally in a distal direction in response to the handle 160 rotating counter-clockwise, or vice versa. The movement of the inward protrusion 161 and the elongate shape of the slot 186 may be described as generally diagonal when viewing the outward surface of the lead receptacle 180. Examples of slots 186 are further described herein (see FIGS. 7 and 8A-D).

As shown, the example sleeve 170 includes a proximal end portion 172, a distal end portion 174, a tapered portion 176, and a flange 178. The lead 106 may extend through the sleeve 170 in the longitudinal direction. In the unlocked position, the sleeve 170 may have a nominal shape that is unconstrained by the lead receptacle 180. The sleeve 170 may be described as a chuck. The distal end portion 174 may define an outer diameter in the unlocked position.

As the handle 160 is rotated by the user, the slot 186 engaging with the inward protrusion 161 encourages the handle 160 to move distally. The sleeve 170 may be encouraged distally in the axial direction via a connection to the handle 160 and may begin to deflect against the inner surface 182 of the lead receptacle 180. The flange 178 of the sleeve may be coupled to the handle 160. For example, the flange 178 may be retained in the channel 163 and form a floating connection. The floating connection may allow the sleeve 170 to freely rotate relative to the handle 160 in the unlocked position. The outer diameter of the distal end portion 174 may decrease the further the sleeve 170 is encouraged distally.

In some embodiments, the floating connection is formed by positioning the sleeve 170 within the opening 166 of the axial portion 162 of the handle 160 without the cap 165. In particular, the flange 178 may be positioned proximally relative to the inward annular protrusion 168. Once the sleeve 170 is in place, the cap 165 may cover the flange 178 of the sleeve 170 and be coupled to the axial portion 162 of the handle 160. For example, the cap 165 may be laser welded or otherwise fixed to the axial portion 162. The coupling of the cap 165 may form a hermetic seal.

In some embodiments, after the floating connection between the handle 160 and the sleeve 170 is formed, the handle 160 is coupled to the lead receptacle 180. The sleeve 170 may be slidably inserted into the opening 188 of the lead receptacle 180. A proximal portion, or nose, of the lead receptacle 180 may be slidably inserted into the axial portion 162 of the handle 160 without the inward protrusion 161. Once the handle 160 and sleeve 170 are in place, the inward protrusion 161 may be inserted through a wall of the axial portion 162 to engage the slot 186 of the lead receptacle 180 and be coupled to the axial portion 162 of the handle 160. For example, the inward protrusion 161 may be laser welded or otherwise fixed to the axial portion 162. The coupling of the inward protrusion 161 may form a hermetic seal.

In the locked position, the distal end portion 174 may engage the shoulder 194 of the collar 192 of the lead 106 in the locked position. The outer diameter of the distal end portion 174 may define an outer diameter in the locked position that is less than the outer diameter in the unlocked position. The shoulder 194 may be axially compressed between the distal end portion 174 and the shoulder 184 of the inner surface 182. A radially compressive force may also be applied to the collar 192 by the sleeve 170. The radially compressive force on the collar 182 by the sleeve 170 may be substantially less than the axially compressive force applied to the shoulder 184. In some embodiments, the sleeve 170 may apply only one of a radially compressive force and an axial force upon the collar 182 of the lead 106.

The force applied to retain the lead 106 is preferably insufficient to cause plastic deformation of either the sleeve 170 or the collar 182. The collar 182 may be formed of a rigid material that does not deform in the locked position. The lead 106 may be retained in the lead connector assembly 150 in the locked position. In the locked position, a hermetic seal may be formed between the sleeve 170, the lead receptacle 180, and the lead 106. In some embodiments, in the locked position, the collar 182 may form at least part of a hermetic seal between the lead sleeve 190 and the sleeve 170 (for example, radially). In some embodiments, in the locked position, the shoulder 194 of the collar 182 may be further form at least part of a hermetic seal between the sleeve 170 and the lead receptacle 180 (for example, axially). In one or more embodiments, the sleeve 170, the collar 182, and the lead receptacle 180 are formed of a metal material.

Due to the resilient material of the sleeve 170, the sleeve may provide an axial back pressure to encourage the handle 160 in a proximal direction relative to the lead receptacle 180.

The lead 106 may be released from the lead connector assembly 150 by the user moving the handle 160 from the locked position to the unlocked position. As the handle 160 is unlocked, the sleeve 170 may be encouraged proximally in the axial direction via the floating connection to the handle 160 and may begin to return from a deflected shape to the nominal shape. In other words, the handle 160 is coupled to the proximal end portion 172 of the sleeve 170 (for example, the flange 178) to move the sleeve axially in both directions (for example, proximally and distally) along the longitudinal axis 20 relative to the lead receptacle 180.

Figure 7:
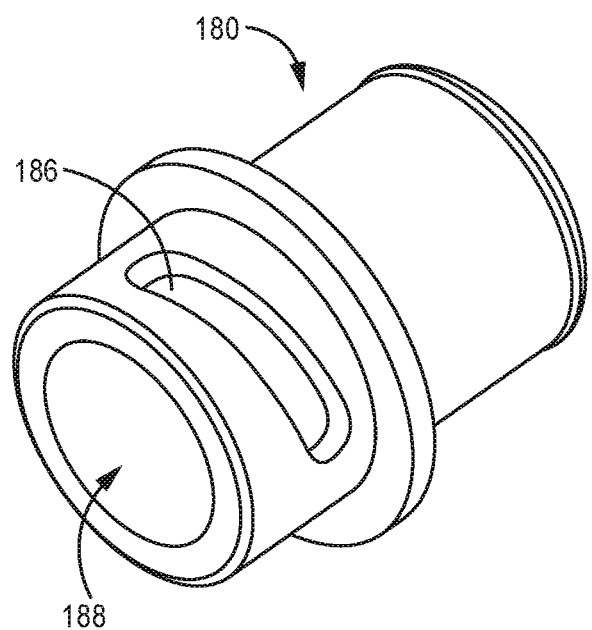
FIG. 7 shows a perspective view of an example lead receptacle of an example lead connector assembly.
Figure 8A:
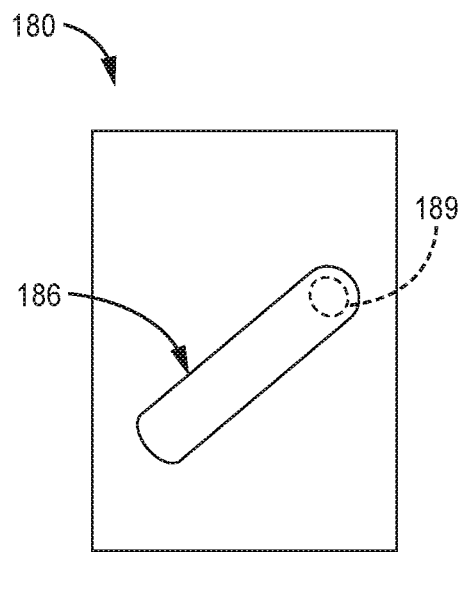
FIGS. 8A-D show flattened projections of example outward surfaces of example lead receptacles.
Figure 8B:
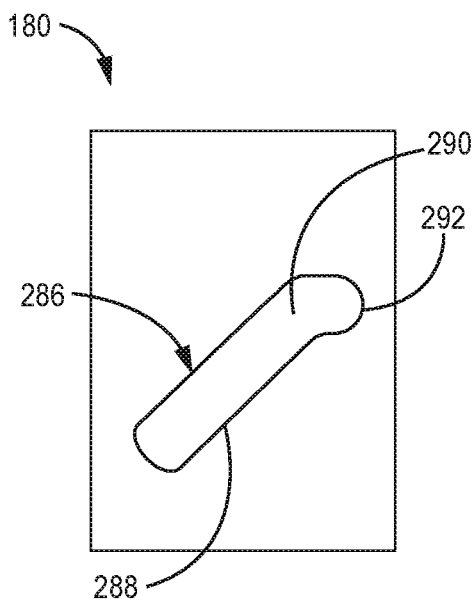
Figure 8C:
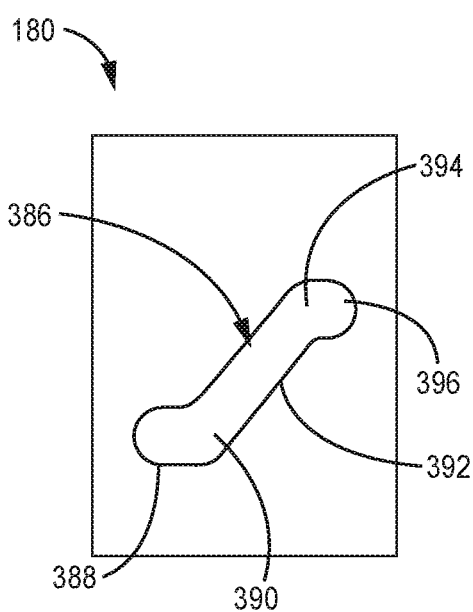
Figure 8D:
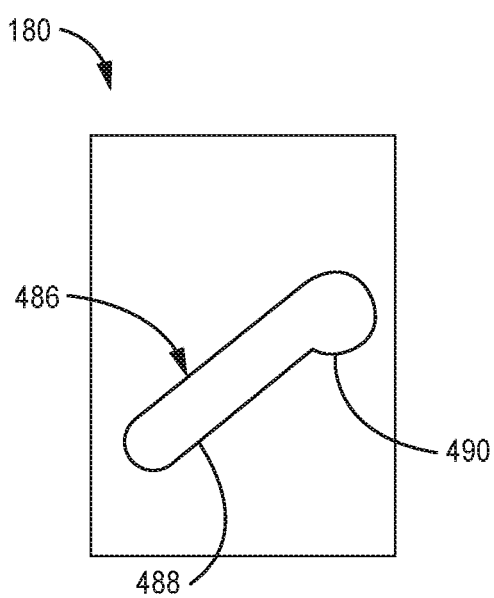

FIG. 7 shows a perspective view of the example lead receptacle 180 including slot 186 and defining an opening 188. FIGS. 8A-D show flattened projections of various slots 186, 286, 386, 486 for illustrative purposes. The flattened projection illustrates a view of the outward surface of the lead receptacle 180 when flattened from its annular shape. In other words, the illustrated shapes of the slots 186, 286, 386, 486 would wrap around the curvature of the lead receptacle 180 as shown in FIG. 7.

The slot 186 has a linear path. The shape of slot 186 may guide the handle 160 axially in a linear fashion as the handle is rotated in either direction between locked and unlocked positions. In other words, the slot 186 extends diagonally. The slot 186 may include an optional recess 189 that extends radially further into the material of the lead receptacle 180 than other portions, or the remainder of, of the slot 186. The recess 189 may be positioned to engage the inward protrusion 161 of the handle 160 (FIGS. 4-6) in the locked position. The recess 189 may be described as a well. The recess 189 may provide retention of the inward protrusion 161 in the locked position.

The slot 286 includes at least one horizontal segment 292 aligned to extend along a plane orthogonal to the longitudinal axis. The slot 286 may have a diagonal segment 288 that may be linear and the horizontal segment 292 connected to the diagonal segment 288 by a bend 290. In the locked position, the inward protrusion 161 may be positioned in the horizontal segment 292. As the inward protrusion 161 of the handle 160 approaches the locked position, the horizontal segment 292 may guide the handle to move rotationally but not axially. The slot 286 may provide a tactile feel for the user feel of approaching and achieving a locked position.

The slot 386 is like the slot 286 but includes another horizontal segment 388 at the other end of the slot. Slot 386 may have a horizontal segment 388, a diagonal segment 392 connected to the horizontal segment 388 by a bend 390, and another horizontal segment 396 connected to the diagonal segment 392 by a bend 394. In the unlocked position, the inward protrusion 161 may be positioned in the horizontal segment 388 (for example, lower left). In the locked position, the inward protrusion 161 may be positioned in the horizontal segment 396 (for example, top right). The slot 386 may provide a tactile feel for the user feel of approaching and achieving a locked position, like slot 286, and also approaching and achieving an unlocked position.

The slot 486 is like slot 186 but includes a different type of recess 490. The slot 486 includes a diagonal segment 488 and a recess 490. The recess 490 may be positioned to engage the inward protrusion 161 of the handle 160 in the locked position. described as a sharp turn or widening of the segment, for example, at least in the distal direction. As the inward protrusion 168 approaches the locked position, the inward protrusion may be encouraged in the proximal direction into the recess 490. For example, the deflectable nature of the sleeve 170 may provide an axial back pressure that encourages the inward protrusion 161 into the recess 490. The slot 486 may provide retention of the inward protrusion 161 in the locked position.

Figure 9:
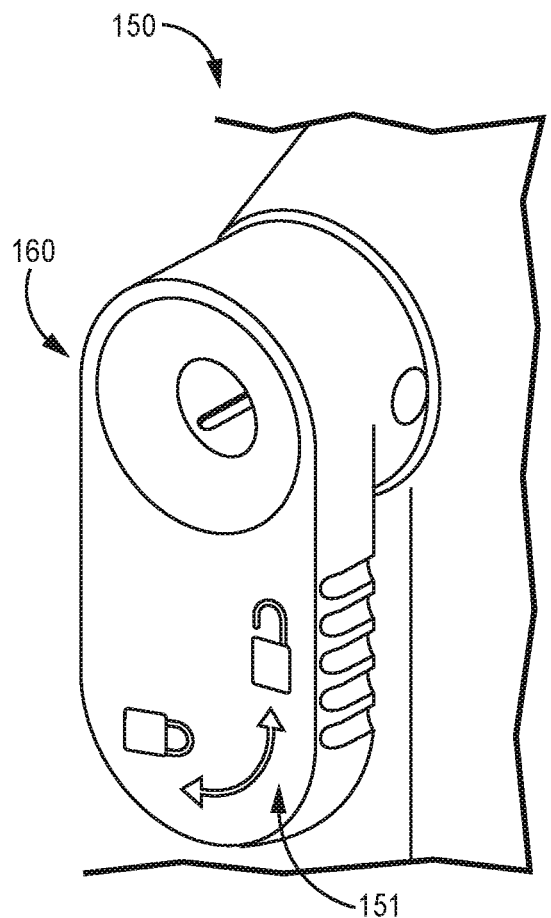
FIG. 9 shows an example visual indicia of an example lead connector assembly.

FIG. 9 shows a perspective view of the example lead connector assembly 150 including indicia 151. The indicia 151 may be visible by the user. The indicia 151 may provide visual instruction for operating the lead connector assembly 150, particularly the direction to move, or rotate, the handle 160 to lock or unlock. As illustrated, a clockwise rotation of the handle 160 may lock and a counter-clockwise rotation may unlock.

Figure 10:
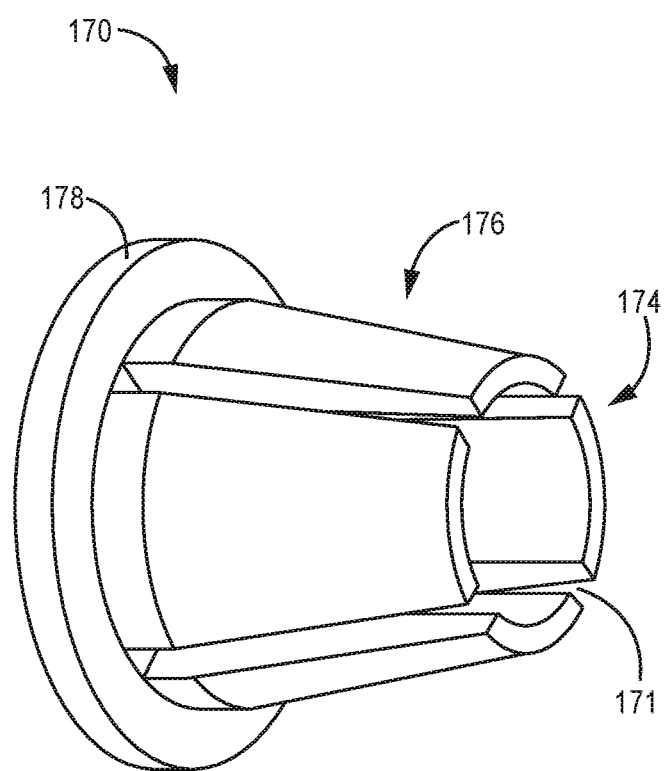
FIG. 10 shows a perspective view of an example sleeve of an example lead connector assembly.

FIG. 10 shows a perspective view of a sleeve 170 of an example lead connector assembly. The sleeve 170 includes a tapered portion 176. The tapered portion 176 may be in the shape of a cone or partial cone. The tapered portion 176 may include one or more longitudinal slits 171 extending through the material. The slits 171 may be described as the absence of material forming the sleeve 170. The slits 171 may provide easy deflection of the tapered portion 176 and the distal portion 174, for example, to a smaller diameter. In the illustrated embodiment, the slits 171 extend the entire length of the tapered portion 176. In other embodiments, one or more slits 171 do not extend the entire length of the tapered portion 176. In the illustrated embodiment, the flange 178 of the sleeve 170 has no slits.

The medical systems of the present disclosure may use the lead connector assembly in various processes to secure the lead to the medical device. The medical systems of the present disclosure include a lead connector assembly coupled to the medical device, which may or may not form a hermetic seal therebetween. The lead may be inserted through the lead connector assembly and into the medical device. The lead connector assembly may then be locked to retain the lead.

Further, the medical systems of the present disclosure include a lead connector assembly slidably coupled to, or kitted with, the lead. The lead and lead connector assembly may be considered disposable or modular. The lead may be inserted into the medical device and the lead connector assembly may be coupled, or fastened, to the medical device (for example, by a set screw). The lead connector assembly may then be locked to retain the lead.

Thus, embodiments of the TOOLLESS LEAD CONNECTOR ASSEMBLY are disclosed. Although reference is made to the accompanying set of drawings that form a part hereof and in which are shown by way of illustration several specific embodiments, it is to be understood that other embodiments are contemplated and may be made without departing from (for example, still falling within) the scope or spirit of the present disclosure. The detailed description, therefore, is not to be taken in a limiting sense.

All scientific and technical terms used herein have meanings commonly used in the art unless otherwise specified. The definitions provided herein are to facilitate understanding of certain terms used frequently herein and are not meant to limit the scope of the present disclosure.

Unless otherwise indicated, all numbers expressing feature sizes, amounts, and physical properties used in the specification and claims are to be understood as being modified in all instances by the term "about." Accordingly, unless indicated to the contrary, the numerical parameters set forth in the foregoing specification and attached claims are approximations that can vary depending upon the desired properties sought to be obtained by those skilled in the art utilizing the teachings disclosed herein.

The recitation of numerical ranges by endpoints includes all numbers subsumed within that range (for example 1 to 5 includes 1, 1.5, 2, 2.75, 3, 3.80, 4, and 5) and any range within that range. Herein, the terms "up to" or "no greater than" a number (for example, up to 50) includes the number (for example, 50), and the term "no less than" a number (for example, no less than 5) includes the number (for example, 5).

The terms "coupled" or "connected" refer to elements being attached to each other either directly (in direct contact with each other) or indirectly (having one or more elements between and attaching the two elements).

Terms related to orientation, such as "axial," "longitudinal," "radial," "lateral," "proximal," "distal," "top", "bottom", "left", "right," and "end", are used to describe relative positions of components and are not meant to limit the orientation of the embodiments contemplated. For example, an embodiment described as having a "top" and "bottom"

also encompasses embodiments thereof rotated in various directions unless the content clearly dictates otherwise.

Reference to "one embodiment," "an embodiment," "certain embodiments," or "some embodiments," etc., means that a particular feature, configuration, composition, or characteristic described in connection with the embodiment is included in at least one embodiment of the disclosure. Thus, the appearances of such phrases in various places throughout are not necessarily referring to the same embodiment of the disclosure. Furthermore, the particular features, configurations, compositions, or characteristics may be combined in any suitable manner in one or more embodiments.

The words "preferred" and "preferably" refer to embodiments of the disclosure that may afford certain benefits, under certain circumstances. However, other embodiments may also be preferred, under the same or other circumstances. Furthermore, the recitation of one or more preferred embodiments does not imply that other embodiments are not useful, and is not intended to exclude other embodiments from the scope of the disclosure.

As used in this specification and the appended claims, the singular forms "a", "an", and "the" encompass embodiments having plural referents, unless the content clearly dictates otherwise.

As used herein, "have", "having", "include", "including", "comprise", "comprising" or the like are used in their open ended sense, and generally mean "including, but not limited to". It will be understood that "consisting essentially of", "consisting of", and the like are subsumed in "comprising," and the like.

The phrases "at least one of," "comprises at least one of," and "one or more of" followed by a list refers to any one of the items in the list and any combination of two or more items in the list.

What is claimed is:

1. A medical device comprising: a lead receptacle comprising an inner surface and defining an opening configured to receive a lead, wherein a portion of the inner surface is tapered; a sleeve deflectable by the inner surface of the lead receptacle, the sleeve comprising a proximal end portion and a distal end portion, the distal end portion defining a first outer diameter to engage the lead in a locked position and a second outer diameter greater than the first diameter in an unlocked position; and a handle movably retained to the lead receptacle and coupled the proximal end portion of the sleeve to move the sleeve axially in both directions along the longitudinal axis relative to the lead receptacle, wherein the sleeve is configured to move axially along the tapered portion of the inner surface of the lead receptacle between the locked and unlocked positions.

2. The medical device according to claim 1, wherein the handle is not removable from the lead receptacle.

3. The medical device according to claim 1, wherein the handle comprises an axial portion defining an opening aligned to the longitudinal axis and a lever portion protruding radially from the axial portion.

4. The medical device according to claim 1, wherein the proximal end portion of the sleeve is retained in a channel of the handle.

5. The medical device according to claim 4, wherein the sleeve comprises a flange and the channel of the handle retains the flange.

6. The medical device according to claim 5, wherein the channel is formed between a cap and an inward annular protrusion to define a floating connection with the flange of the sleeve.

7. The medical device according to claim 1, wherein the lead receptacle limits rotation of the handle beyond at least one of the locked and unlocked positions.

8. The medical device according to claim 7, wherein the handle rotates no more than about 90 degrees between locked and unlocked positions.

9. The medical device according to claim 1, wherein the lead receptacle defines an outward slot and the handle comprises an inward protrusion configured to engage and slide along the outward slot.

10. The medical device according to claim 9, wherein the outward slot comprises at least one segment aligned to extend along a plane orthogonal to the longitudinal axis.

11. The medical device according to claim 9, wherein the outward slot comprises a recess to retain the inward protrusion in the locked position.

12. The medical device according to claim 11, wherein the sleeve provides axial back pressure to encourage the inward protrusion into the recess.

13. The medical device according to claim 1, wherein the sleeve includes a tapered portion with at least one longitudinal slit.

14. A medical system comprising:
a lead comprising a lead sleeve and a collar fixed to the lead sleeve;
a lead receptacle defining an opening configured to receive the lead, the lead receptacle comprising an inner surface;
a sleeve deflectable by the inner surface of the lead receptacle, the sleeve comprising a proximal end portion and a distal end portion, the distal end portion defining a first outer diameter to engage the collar of the lead in a locked position and a second outer diameter greater than the first diameter in an unlocked position; and
a handle coupled to the lead receptacle and the proximal end portion of the sleeve to move the sleeve axially in both directions along the longitudinal axis relative to the lead receptacle.

15. The medical device according to claim 14, further comprising a housing and at least one of: a set screw to retain the lead receptacle within the housing and a hermetic seal between the lead receptacle and the housing.

16. The medical device according to claim 14, further comprising a housing integrally formed with the lead receptacle.

17. The medical device according to claim 14, further comprising another lead receptacle configured to receive another lead.

18. The medical device according to claim 14, wherein the collar comprises a rigid material.

19. The medical device according to claim 14, wherein the collar comprises a shoulder protruding between the sleeve and the lead receptacle in the locked position.

20. A medical system comprising:
a lead receptacle defining an opening, the lead receptacle comprising an inner surface, wherein a portion of the inner surface is tapered;
a lead comprising a lead sleeve extending through the opening and a collar fixed to the lead sleeve;
a sleeve deflectable by the inner surface of the lead receptacle and comprising a proximal end portion and a distal end portion defining a first outer diameter to engage the lead in a locked position and a second outer diameter greater than the first diameter in an unlocked position; and a handle coupled to the lead receptacle and the proximal end portion of the sleeve to move the sleeve axially in both directions along the longitudinal axis relative to the lead receptacle, wherein the sleeve is configured to move axially along the tapered portion of the inner surface of the lead receptacle such that the distal end portion of the sleeve changes between the first outer diameter and the second outer diameter.

* * * * *